US010702617B2

(12) United States Patent
Weeks, Jr. et al.

(10) Patent No.: US 10,702,617 B2
(45) Date of Patent: Jul. 7, 2020

(54) ANTIMICROBIAL BACKLIT DEVICE

(71) Applicant: Hubbell Incorporated, Shelton, CT (US)

(72) Inventors: Thomas Warren Weeks, Jr., Simpsonville, SC (US); Thomas James Veltri, Simpsonville, SC (US); John Lawrence Wolf, Crystal Lake, IL (US); Blake Ashton Nickles, Greenville, SC (US); Christopher Lane Bailey, Greenville, SC (US)

(73) Assignee: Hubbell Incorporated, Shelton, CT (US)

( * ) Notice: Subject to any disclaimer, the term of this patent is extended or adjusted under 35 U.S.C. 154(b) by 0 days.

(21) Appl. No.: 16/174,937

(22) Filed: Oct. 30, 2018

(65) Prior Publication Data

US 2019/0125905 A1 May 2, 2019

Related U.S. Application Data

(60) Provisional application No. 62/578,753, filed on Oct. 30, 2017.

(51) Int. Cl.
*G09F 13/04* (2006.01)
*A61L 2/08* (2006.01)
(Continued)

(52) U.S. Cl.
CPC ............... *A61L 2/084* (2013.01); *A61L 2/24* (2013.01); *G06K 9/00087* (2013.01);
(Continued)

(58) Field of Classification Search
CPC . A61L 2/084; A61L 2/085; A61L 2/10; A61L 2202/14; G09F 13/04; G09F 13/08
(Continued)

(56) References Cited

U.S. PATENT DOCUMENTS

| 3,926,556 A | 12/1975 | Boucher |
| 4,910,942 A | 3/1990 | Dunn et al. |

(Continued)

FOREIGN PATENT DOCUMENTS

| JP | 2004301387 | 10/2004 |
| JP | 2007232323 | 9/2007 |

(Continued)

OTHER PUBLICATIONS

Maclean et al., "405 nm light technology for the inactivation of pathogens and its potential role for environmental disinfection and infection control," *The Journal of Hospital Infection*, Sep. 2014, vol. 88, Issue 1—27 pages.

(Continued)

*Primary Examiner* — Thuy V Tran
(74) *Attorney, Agent, or Firm* — Michael Best & Friedrich, LLP

(57) ABSTRACT

Antimicrobial backlit devices and methods are provided. In one example embodiment, a device includes a backlight system configured to provide backlight for a display screen of the device. The backlight system includes one or more HINS light sources configured to emit HINS light and one or more non-HINS light sources configured to emit non-HINS light. The device further includes one or more control devices configured to control operation of the one or more HINS light sources and the one or more non-HINS light sources according to one or more light control profiles.

8 Claims, 11 Drawing Sheets

(51) Int. Cl.
*A61L 2/24* (2006.01)
*G06K 9/00* (2006.01)
*H05B 45/20* (2020.01)
*H05B 47/105* (2020.01)
*G09F 13/06* (2006.01)
*A61L 2/10* (2006.01)

(52) U.S. Cl.
CPC ........... *H05B 45/20* (2020.01); *H05B 47/105* (2020.01); *A61L 2/085* (2013.01); *A61L 2/10* (2013.01); *A61L 2202/122* (2013.01); *A61L 2202/14* (2013.01); *A61L 2202/24* (2013.01); *G09F 13/04* (2013.01); *G09F 13/06* (2013.01)

(58) Field of Classification Search
USPC ....................... 345/102; 362/97.1, 97.2, 97.3
See application file for complete search history.

(56) References Cited

U.S. PATENT DOCUMENTS

| | | |
|---|---|---|
| 6,251,127 B1 | 6/2001 | Biel |
| 8,398,264 B2 | 3/2013 | Anderson et al. |
| 9,039,966 B2 | 5/2015 | Anderson et al. |
| 9,333,274 B2 | 5/2016 | Peterson et al. |
| 9,439,989 B2 | 9/2016 | Lalicki |
| 9,642,356 B2 | 5/2017 | Wood et al. |
| 9,642,358 B2 | 5/2017 | Cai et al. |
| 9,700,641 B2 | 7/2017 | Hawkins et al. |
| 9,927,097 B2 | 3/2018 | Lalicki et al. |
| 2002/0074559 A1 | 6/2002 | Dowling et al. |
| 2003/0137258 A1 | 7/2003 | Piepgras et al. |
| 2004/0039242 A1 | 2/2004 | Tolkoff et al. |
| 2004/0141321 A1 | 7/2004 | Dowling et al. |
| 2005/0049228 A1 | 3/2005 | Albrecht et al. |
| 2005/0055070 A1 | 3/2005 | Jones et al. |
| 2005/0107849 A1 | 5/2005 | Altshuler et al. |
| 2006/0085052 A1 | 4/2006 | Feuerstein et al. |
| 2006/0221606 A1 | 10/2006 | Dowling et al. |
| 2008/0137066 A1 | 6/2008 | Weinstein |
| 2009/0076115 A1 | 3/2009 | Wharton et al. |
| 2009/0168396 A1 | 7/2009 | Moriyasu et al. |
| 2010/0208054 A1 | 8/2010 | Farr |
| 2010/0246169 A1* | 9/2010 | Anderson ............... A61L 2/084 362/231 |
| 2010/0259917 A1 | 10/2010 | Ramer et al. |
| 2011/0180687 A1 | 7/2011 | Rains, Jr. et al. |
| 2011/0227487 A1 | 9/2011 | Nichol et al. |
| 2011/0256019 A1* | 10/2011 | Gruen ....................... A61L 2/10 422/24 |
| 2013/0291735 A1 | 11/2013 | Livchak et al. |
| 2013/0293156 A1 | 11/2013 | Wells |
| 2014/0060096 A1 | 3/2014 | Shur |
| 2014/0278136 A1 | 9/2014 | Shamsheyeva et al. |
| 2015/0002027 A1 | 1/2015 | Huang |
| 2015/0273092 A1 | 10/2015 | Holub et al. |
| 2016/0015840 A1* | 1/2016 | Gordon ................. A61L 2/0052 422/22 |
| 2016/0030609 A1 | 2/2016 | Peterson et al. |
| 2016/0030610 A1 | 2/2016 | Peterson et al. |
| 2016/0120410 A1* | 5/2016 | Kim ....................... G01J 3/0227 356/418 |
| 2016/0339203 A1 | 11/2016 | Krames et al. |
| 2016/0361229 A1 | 12/2016 | Na |
| 2016/0375161 A1 | 12/2016 | Hawkins |
| 2016/0375162 A1 | 12/2016 | Marry |
| 2016/0375163 A1 | 12/2016 | Hawkins et al. |
| 2017/0006685 A1 | 1/2017 | Barron et al. |
| 2017/0034889 A1 | 2/2017 | Primous et al. |
| 2017/0080117 A1* | 3/2017 | Gordon ................. A61L 2/0052 |
| 2017/0101326 A1 | 4/2017 | Zhou |
| 2017/0101328 A1 | 4/2017 | Smetona et al. |
| 2018/0121703 A1* | 5/2018 | Jung ..................... G06K 9/0004 |
| 2018/0225498 A1* | 8/2018 | Setlak ................ G06K 9/00026 |

FOREIGN PATENT DOCUMENTS

| | | |
|---|---|---|
| WO | WO2007012875 | 2/2007 |
| WO | WO 2009/056838 | 5/2009 |

OTHER PUBLICATIONS

Maclean et al., "An Innovation: Decontamination by Light—HINS-light Environmental Decontamination System, a new method for pathogen control in the clinical environment," Microsoft Power Point, HINS-light EDS Presentation for Infection Prevention Scotland, The Robertson Trust Laboratory for Electronic Sterilisation Technologies (ROLEST), Oct. 27, 2010—20 pages.

Noimark et al., "Light-activated antimicrobial surfaces with enhanced efficacy induced by a dark-activated mechanism," *Chemical Science*, Issue 6, Jun. 1, 2014—1 page.

Wallace, John "HINS light kills surface bacteria in hospitals," Laser Focus World, http://www.laserfocusworld.com/articles/2010/11/hins-light-kills-surface.html, accessed on Oct. 30, 2017, PennWell Corporation, Tulsa, OK, Nov. 15, 2010—2 pages.

Maclean et al., "Environmental decontamination of a hospital isolation room using high-intensity narrow-spectrum light," *The Hospital Infection Society*, Elsevier Ltd., Nov. 2010;76(3)—1 page.

Kermit Mfg. Launches New Bacteria-killing LED Light for Hospitals, LEDinside, a Business Division of TrendForce Corp., Jun. 29, 2015, accessed on Oct. 30, 2017, http://www.ledinside.com/products/2015/6/kenall_manufacturing_launches_new_uv_led_light_for_hospitals—3 pages.

PCT International Search Report and Written Opinion for corresponding PCT Application No. PCT/US2018/058188, dated Feb. 19, 2019, 13 pages.

Nitzan et al. "ALA induced photodynamic effects on Gram positive and negative bacteria," *Photochem. Photobiol. Sci.*, 2004, 3—18 pages.

Maclean "An Investigation Into the Light Inactivation of Medically Important Microorganisms," University of Strathclyde, 2006—260 pages.

Nitzan et al., "Endogenous Porphyrin Production in Bacteria by Aminolaevulinic Acid and Subsequent Bacterial Photoeradication," *M. Lasers Med Sci* (Dec. 1999) vol. 14, Issue 4, pp. 269-277.

Ashkenazi et al., "Eradication of Propionibacterium acnes by its endogenic porphyrins after illumination with high intensity blue light," *FEMS Immunology & Medical Microbiology*, vol. 35, Issue 1, Jan. 1, 2003, pp. 17-24.

Ganz et al., "*Helicobacter pylori* in Patients Can Be Killed by Visible Light," *Lasers Surg Med.*, Apr. 2005; 36(4): pp. 260-265.

Møller et al., "How Finsen's light cured lupus vulgaris," *Photodermatol Photoimmunol Photomed* 2005; 21: pp. 118-124.

Kjeldstad, "Photoinactivation of Propionibacterium acnes by Near-Ultraviolet Light," *Zeitschrift fur Naturforschung C*, vol. 39, Issue 3-4, 1984, pp. 300-302.

Derosa et al., "Photosensitized singlet oxygen and its applications," *Coordination Chemistry Reviews*, vols. 233-234, Nov. 1, 2002, pp. 351-371.

Elman et al., "The effective treatment of acne vulgaris by a high-intensity, narrow band 405-420 nm light source," *J Cosmetic & Laser Ther* 2003; 5: pp. 111-116.

Konig et al., "Red Light Kills Bacteria via Photodynamic Action," Abstract, *Cellular and molecular biology*, 46(7):1297-303, Dec. 2000—1 page.

Philipp-Dormston et al., "Comparison of Porphyrin and Heme in Various Heterotrophic Bacteria," Abstract, *Enzyme* 16(1):57-64 • Feb. 1973—1 page.

* cited by examiner

ANTIMICROBIAL BACKLIT DEVICE

PRIORITY CLAIM

The present application is based on and claims priority to U.S. Provisional Application No. 62/578,753, titled "Antimicrobial Backlit Device," having a filing date of Oct. 30, 2017, which is incorporated by reference herein.

FIELD

The present subject matter relates generally to backlit devices.

BACKGROUND

Light sources can be used to provide illumination for display devices such as liquid crystal display (LCD) devices, LED display devices, OLED display devices, plasma display devices through backlighting, front lighting and edge lighting techniques. The display devices can be implemented within, or otherwise associated with a variety devices, such as computer monitors, televisions, laptop computers, desktop computers, smartphones, tablets, wearable computing devices, touch panels, point of sale devices, gaming devices, and lighting control interfaces. Often, display devices collect microbes on surfaces with which humans interact.

SUMMARY

Aspects and advantages of embodiments of the present disclosure will be set forth in part in the following description, or may be learned from the description, or may be learned through practice of the embodiments.

One example aspect of the present disclosure is directed to an electronic device. The electronic device can include a display screen. The electronic device can further include one or more high intensity narrow spectrum (HINS) light sources. The one or more HINS light sources can be configured to emit HINS light onto the display screen.

Another example aspect of the present disclosure is directed to a method for providing HINS light onto a display screen of a display device. The method includes receiving, by one or more processors of a control system for the display device, a light activation signal. The method further includes accessing, by the one or more processors, data associated with a light control profile. The method includes controlling, by the one or more processors, operation of one or more HINS light sources of the display device to dose the display screen with HINS light according to the light control profile.

Yet another example aspect of the present disclosure is directed to a HMI device. The HMI device includes a biometric sensor. The HMI device further includes one or more HINS light sources configured to emit light onto the biometric sensor.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
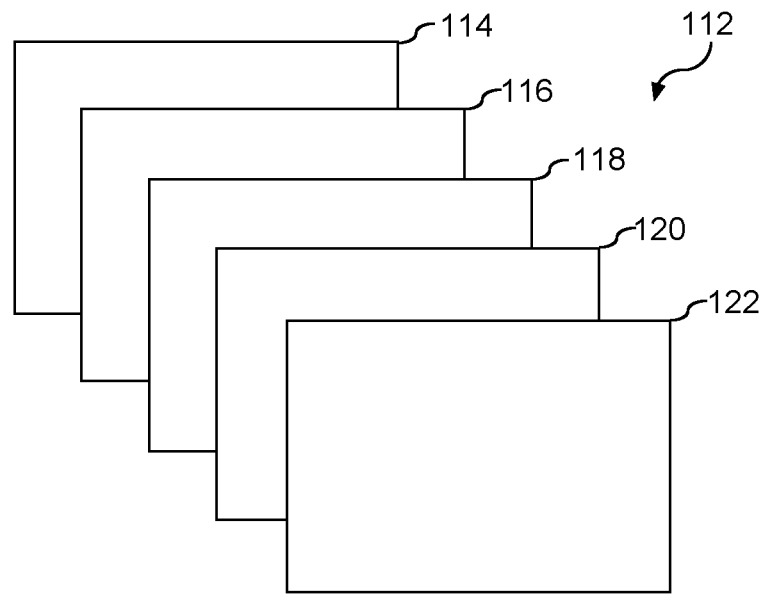
FIG. 1 depicts an overview of an example display device according to example embodiments of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

One example aspect of the present disclosure is directed to systems and methods of providing antimicrobial lighting in conjunction with a display device, such as display screens associated with a computer monitor, television, laptop, desktop, smartphone, tablet, wearable computing device, touch panel, point of sale device, gaming device, lighting control interface, touch sensors (e.g., biometric sensors) etc. For instance, a display device associated with an electronic device can include a light source having one or more lighting elements configured to illuminate the display. According to particular aspects of the present disclosure, the light source can include one or more lighting elements configured to emit a high intensity narrow spectrum (HINS) light. In some embodiments, the light source can additionally include one or more lighting elements configured to emit a visible light not within the HINS spectrum (e.g. white light, blue light, etc.).

The HINS light can be light having a peak wavelength in the range of about 380 nanometers (nm) to about 420 nm, such as 400 nm to 420 nm. In some implementations, the HINS light can be about 405 nm. As will be understood by those skilled in the art, using the disclosures provided herein, the HINS light can provide antimicrobial qualities to surfaces upon which the light is emitted. In this manner, the HINS light can reduce, eliminate, suppress and/or inactivate bacterial, fungal, viral, and/or other microorganism contamination on such surfaces.

In some embodiments, the antimicrobial lighting system can further include one or more control devices (e.g., processors configured to execute instructions, microcontrollers, logic devices, application specific integrated circuits, etc.). The one or more control devices can be configured to control operation of the light source and display screen in accordance with one or more predefined light control profiles. The light control profiles can specify one or more time periods during which the HINS light is to be emitted by the light source and/or one or more time periods during which the HINS light is not emitted by the light source.

As one example embodiment, a device can include a LCD display screen. The LCD display screen can include, for instance, an LCD layer, a glass substrate, a light source layer, and/or other layers. The LCD layer can include a plurality of pixels. Each pixel can transmit light through liquid crystals. The orientation of the liquid crystals relative to the light source can be controlled by an electric field to provide varying images on the display. The light source can include one or more HINS light sources configured to emit HINS light. For instance, the light source can include one or more HINS light emitting diodes (LEDs). The light source can be configured to periodically emit HINS light though the LCD layer to provide an antimicrobial function for reducing microbes on the LCD display screen.

Example aspects of the present disclosure are discussed with referenced to an LCD screen for purposes of illustration and discussion. Those of ordinary skill in the art, using the disclosures provided herein, will understand that example aspects of the present disclosure can be used with other display screens, such as LED screen, OLED screens, plasma screens, etc.

In some implementations, the light source can be configured to provide backlighting for a display device in accordance with various suitable backlighting techniques. In some implementations, edge-lit backlighting techniques can be used wherein the light source including one or more HINS lighting elements is positioned around a rim or edge of the display device. Full array backlighting techniques can be used where HINS lighting elements are positioned behind the display device. Dynamic local dimming backlighting techniques can be used where the light sources are controlled individually (or in clusters) to control the level of light and/or color intensity in a given part of the display device.

In some implementations, a light source including one or more HINS lighting elements can be a separate and distinct device from the device. For instance, a light source including HINS lighting elements can be attached to an exterior portion of the device. As a particular example, in such implementations, the lighting source can be implemented as a part of casing configured to encompass at least a portion of the device. In this manner, the light source including one or more HINS lighting elements can be configured to emit HINS light onto at least a portion of the device when the casing is positioned around the device. In some embodiments, the casing can be removable from the device.

In some implementations, the display device can additionally include one or more antimicrobial materials configured to reduce, eliminate, and/or inactivate bacterial, fungal, viral, and/or other microorganism contamination on the surface of the display. In such implementations, the antimicrobial qualities of the display device can be combined with the antimicrobial qualities of the HINS light to reduce, eliminate, suppress and/or inactivate such contamination.

A light source configured to emit light onto or through a display screen according to example embodiments of the present disclosure can include, or can otherwise be associated with, a control system having one or more control devices configured to control operation of the light source. In particular, the control system can control operation of the light source in accordance with one or more predefined light control profiles. The light control profile(s) can specify one or more time periods during which HINS light is to be emitted by the light source and/or one or more time periods during which the HINS light is not emitted. For instance, a light control profile can specify a first time period during which the HINS light is to be emitted, and a second time period during which non-HINS light is to be emitted and/or during which the HINS light is not to be emitted. The light control profile(s) can further specify one or more time periods during which the non-HINS light is to be emitted.

In some implementations, the time periods specified by the light control profile(s) can be predefined. In some implementations, the time periods can be determined based at least in part on a state of the device. For instance, the time periods can be determined such that HINS light is emitted while the device is activated and/or other state (e.g., in a sleep mode or reduced power state). In some implementations, the time periods can be determined based at least in part on an interaction of a user with the device. As an example, a light control profile can specify that the HINS light is to be emitted during a period of inactivity of the device. For instance, the light control profile can specify that the HINS light should be emitted during a period of time wherein the device is "idle" or otherwise not in use by a user. In some implementations, the light control profile can specify that the HINS light is to be emitted while a screen saver is in use by the device. In this manner, emission of the HINS light can be triggered by the inactivity of the device.

In some implementations, emission of the HINS light can be triggered by the presence of a user proximate the device. In such implementations, the antimicrobial lighting system and/or device can include one or more sensors configured to detect such presence. For instance, the one or more sensors can include one or more motion sensors, position sensors, acoustic sensors, infrared sensors, temperature sensors, electronic eye sensors, biomedical sensors, accelerometers, gyroscopes, or any sensors that are suitable to detect whether an area is occupied by a human or other user and/or whether a user is using the device.

In some implementations, emission of the HINS light can be triggered when something is placed over the display device. For instance, the HINS light can be triggered when the display device is covered by a surface (e.g., by being placed face down on a surface and/or when a case or other cover is positioned over the display device). In this way, HINS light can be emitted only when the display screen is not in view.

Another example aspect of the present disclosure is directed to a human machine interface (HMI) device. The HMI device can be used to control access to an area. For instance, the HMI device can be associated with a door that is used to enter and exit a room. Alternatively, the HMI device can be used to control access to a device, such as an automated teller machine (ATM).

The HMI device can include a biometric sensor configured to obtain a biometric trait (e.g., fingerprint) of a user attempting to gain access to the area or device to which access is controlled by the HMI device. The biometric trait can be used to determine an identity of the user. The HMI device can include one or more control devices configured to determine whether the person is authorized to access the area or device based, at least in part, on the biometric trait obtained via the biometric sensor.

In some implementations, the HMI device can include a keypad. The keypad can include a plurality of buttons. In this manner, users can manipulate the plurality of buttons to enter a credential (e.g., passcode) needed to gain access to the area or device to which access is controlled by the HMI device. In alternative implementations, the HMI device can include a touch-screen configured to display a keypad. In this manner, users can manipulate (e.g., touch) one or more buttons of the keypad displayed on the touch-screen to enter the credential needed to gain access to the device or area.

The HMI device can include one or more HINS light sources configured to emit HINS light onto a surface of the biometric sensor users must touch while the biometric sensor is obtaining the biometric trait. In this manner, microbes present on the surface of the biometric sensor can be inactivated via the HINS light. In some implementations, the HMI device can include one or more HINS light sources configured to emit light onto the keypad. In this manner, microbes present on the plurality of buttons of the keypad can be inactivated via the HINS light.

In some implementations, the HMI device can include one or more non-HINS light sources configured to emit non-HINS light onto the surface of the biometric sensor. In this manner, the surface of the biometric sensor can be illuminated via the non-HINS light. Additionally, the HMI device can include one or more non-HINS light sources configured to emit non-HINS light onto the plurality of buttons of the keypad. In this manner, the plurality of buttons can be illuminated via the non-HINS light.

In some implementations, the HMI device can include one or more control device configured to control operation of the one or more HINS light sources. Additionally, the one or more control devices can be configured to control operation of the one or more non-HINS light sources. In some implementations, the one or more control devices can activate (e.g., turn on) the one or more HINS light sources when a user is not present. For example, the one or more control devices can be configured to activate the one or more HINS light sources when data obtained from one or more motion sensors of the HMI device indicates a user is not present.

When the data obtained from the one or more motion sensors indicate a user is present, the one or more control devices can be configured to deactivate (e.g., turn off) the one or more HINS light sources. In some implementations, the one or more control devices can be further configured to activate (e.g. turn on) the one or more non-HINS light sources when the data indicates a user is present. In addition, the one or more non-HINS light sources can remain activated (e.g., turned on) until the one or more control devices determine a threshold amount of time has lapsed since the one or more motion sensors last detected presence of the user. When this occurs, the one or more control devices can be configured to activate the one or more HINS light sources such that a blend of HINS light and non-HINS light is emitted onto the surface of the biometric sensor and/or the keypad for a predetermined amount of time. Once the predetermine amount of time has lapsed, the one or more control devices can deactivate (e.g., turn off) the one or more non-HINS light sources.

In some implementations, emission of the HINS light can be triggered when something is placed over the surface of the biometric sensor. For instance, the HINS light can be triggered when the surface of the biometric sensor is covered by a surface (e.g., by being placed face down on a surface and/or when a case or other cover is positioned over the surface of the biometric sensor). In this way, HINS light can be emitted only when the surface of the biometric sensor is not in view.

In some implementations, emission of the HINS light can be triggered when something is placed over the keypad. For instance, the HINS light can be triggered when the keypad is covered by a surface (e.g., when a case or other cover is positioned over the plurality of buttons). In this way, HINS light can be emitted only when the keypad is not in view.

As used herein, HINS light refers to light having a peak wavelength in the range of about 380 nanometers (nm) to about 420 nm, such as about 400 nm to about 420 nm, such as about 405 nm. Non-HINS light refers to light in the visible spectrum, but not in the HINS range of about 380 nm to about 405 nm. As used herein, the use of the term "about" in conjunction with a numerical value refers to within 2.5% of the stated numerical value.

With reference now to the figures, example aspects of the present disclosure will be discussed in greater detail. For instance, FIG. 1 depicts an overview of an example display device 112 according to example embodiments of the present disclosure. The display device 112 can be, for instance, an LCD display device. Display device 112 includes a light source 114. Light source 114 can include one or more lighting elements. For instance, light source 114 can include one or more HINS lighting elements (e.g., HINS LEDs) and one or more non-HINS lighting elements (e.g., non-HINS LEDs). The one or more lighting elements can be configured to provide backlighting for the display device 112 in accordance with one or more suitable backlighting techniques. Display device 116 further includes polarizing layers 116 and 122. Polarizing layers 116 and 122 can be oriented perpendicularly with respect to each other. For instance, polarizing layer 116 can be oriented along a vertical axis and polarizing layer 122 can be oriented along a horizontal axis. As will be understood by those skilled in the art, polarizing layers 116 and 122 can be configured to permit light of a specific polarization to pass, and to block light of other polarizations.

Display device 112 further includes a liquid crystal layer 118. The liquid crystal layer 118 can include a plurality of liquid crystals (e.g., nematic liquid crystals), each positioned between two electrodes. A voltage can be applied to the electrodes to align the liquid crystals in different directions. In this manner, the liquid crystals can be configured based at least in part on the orientations of the polarizing layers 116 and 122. Display device 112 further includes a color filter layer 120. Color filter 120 can include a plurality of red, blue, and green filters configured to pass wavelengths of light associated with the respective filter colors. Each color filter can be positioned in front of a liquid crystal element.

Light (e.g., HINS light and/or non-HINS light) emitted by light source 114 can pass through polarizing layer 116, thereby polarizing the emitted light in the direction of the polarizing layer 116. The polarized light can then pass through the liquid crystal layer 118. When a suitable voltage is applied to the electrodes associated with a liquid crystal in the liquid crystal layer 118, the liquid crystal can "untwist" causing light to pass through the liquid crystal unchanged (e.g., to remain vibrating in the direction of the polarizing layer 116). The light can then be filtered by the color filter of the color filter layer 120 positioned in front of the liquid crystal, such that only light having a suitable wavelength passes through the color filter. The light can then travel to polarizing layer 122. Because no light is vibrating in the direction of the polarizing layer 122 (because the liquid crystals were untwisted and the light passed through the liquid crystal layer 118 unchanged), no light passes through the polarizing layer 122.

When no voltage is applied to the electrodes associated with a liquid crystal in the liquid crystal layer 118, the liquid crystal "twists," causing light passing through the liquid crystal to rotate, for instance, 90 degrees. The rotated light then passes through the color filter 120, and on to the polarizing layer 122. Because the rotated light is vibrating in the direction of the polarizing filter 122, it is able to pass through the polarizing filter 122. In this manner, light displayed by the display device 112 can be controlled by applying suitable voltages to each liquid crystal (e.g., to the electrodes associated with the respective liquid crystals) in order to modulate the direction of the light passing through the respective liquid crystals to produce a suitable display configuration. The applied voltages can be controlled, for instance, by one or more switching devices, such as one or more thin film transistors associated with the electrodes. When HINS light is emitted by the light source 114 in accordance with example aspects of the present disclosure, the HINS light can remove, reduce, suppress, and/or inactivate microorganisms on an outer surface of the display device 112.

It will be appreciated that the display device 112 is intended for example purposes only. In this manner, it will be appreciated that various other suitable display devices can be used without deviating from the scope of the present disclosure. For instance, display devices can be used having one or more additional or different components, such as one or more glass layers, one or more additional polarizing layers, one or more insulation layers and/or other suitable components.

Figure 2:
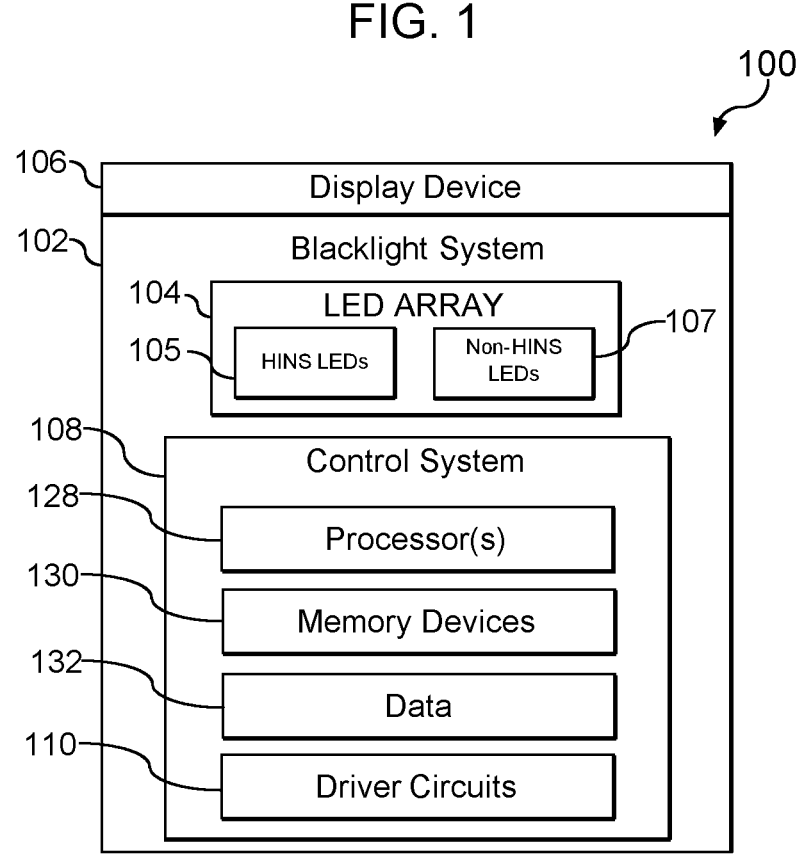
FIG. 2 depicts an overview of an example device according to example embodiments of the present disclosure.

FIG. 2 depicts an overview of an example device 100 according to example embodiments of the present disclosure. Device 100 can be, can be implemented within, or can otherwise be associated with a television, monitor, laptop computing device, desktop computing device, wearable computing device, touch panel, kiosk, gaming device, point of sale device, and/or other suitable device. In some implementations, the device can be or can include an I/O device, such as a keyboard, mouse, touch pad, track-wheel, track-pad, stylus, biometric scanner, or other suitable I/O device.

Device 100 can include a display device 106 and a backlight system 102. Display device 106 can be an LCD display device, or other suitable display device. In some implementations, display device 106 can correspond to display device 112 of FIG. 1. Display device 106 can be a touch-enabled display device configured to receive inputs from a user through contact with a touch panel of the display device 106 by the user or other suitable input mechanism (e.g., stylus, finger, etc.). Backlight system 102 includes an LED array 104. LED array 104 can include a plurality of LEDs arranged in various suitable manners with respect to the display device 106, for instance, to provide backlighting for the display device 106. In particular, LED array 104 can include one or more HINS LEDs 105 configured to emit HINS light and one or more non-HINS LEDs 107 configured to emit non-HINS light. The HINS LEDs 105 can be configured to emit HINS light or can include one or more coatings, lenses, materials, etc. that transform light emitted by the LED devices into HINS light. The non-HINS LEDs 107 can be white LEDs and/or RGB LEDs, and/or other LEDs configured to emit non-HINS light. In alternative implementations, other suitable lighting elements (e.g., cold cathode fluorescent lamps, hot cathode fluorescent lamps, electroluminescent lighting elements, external electrode fluorescent lamps, etc.) can be used.

As indicated, the LEDs of LED array 104 can be arranged to illuminate at least a portion of the display device 106. For instance, the HINS LEDs 105 and the non-HINS LEDs 107 can be arranged to provide backlight to the display device 106 using various suitable backlighting techniques (e.g., edge-lit, bottom-lit, full array, local dimming, etc.). In this manner, the LEDs can be arranged with respect to the display device 106 such that the LEDs can emit light proximate the display device 106 in accordance with such backlighting techniques. In some implementations, the LEDs can be positioned such that the LEDs can emit light proximate the display device 106 to illuminate one or more different portions of the display device 106.

Backlight system 102 can be any suitable backlight system. In this manner, it will be appreciated that backlight system 102 can include various suitable components to facilitate a provision of light to the display device 106. For instance, the backlight system 102 can include various diffuser plates, optical sheets, mixing optics, etc.

Backlight system 102 can further include a control system 108. Control system 108 can include one or more control devices. Control system 108 can be configured to control operation of the lighting array. As shown, control system 108 can include one or more processors 128 and one or more memory devices 130. The one or more processors 128 can include any suitable processing device, such as a microprocessor, microcontroller, integrated circuit, logic device, application specific integrated circuit, or other suitable processing device. The one or more memory devices 130 can include one or more computer-readable media, including, but not limited to, non-transitory computer-readable media, RAM, ROM, hard drives, flash drives, or other memory devices. The one or more memory devices 130 can store information accessible by the one or more processors 128, including computer-readable instructions that can be executed by the one or more processors 128. The instructions can be any set of instructions that when executed by the one or more processors 128, cause the one or more processors 128 to perform operations, such as operations to implement the systems and methods described herein. The one or more memory devices 130 can also store data 132 that can be retrieved, manipulated, created, or stored by the one or more processors 128. The data 132 can include, for instance, light control profile data, and other data.

In some embodiments, control system 108 can be configured to control operation of one or more driver circuits 110 associated with backlight system 102. The one or more driver circuits can be any suitable circuit configured to provide a suitable current to power and/or illuminate the LEDs of LED array 104. In some implementations, each driver circuit 110 can be configured to drive an individual LED. In some implementations, at least one driver circuit can be configured to drive multiple LEDs. The control system 108 can be configured to control operation of driver circuits 110 such that the driver circuits 110 supply suitable currents to the LED array 104. In particular, the driver circuits 110 can be configured to receive an input power, such as an input AC power or an input DC power, and to convert the input power to a suitable output current for powering the LED array 104. The input power can be provided, for instance, by a power supply (not shown) (e.g., a battery) associated with the display device 106 and/or the backlight system 102. For instance, such power supply can be configured to provide suitable power to various components of the backlight system 102 and/or the display device 106. Driver circuits 110 can include various suitable driver circuits and can include various components, such as switching elements (e.g. transistors) that are controlled to provide a suitable output current. For instance, in one embodiment, driver circuit 110 can include one or more transistors. Gate timing commands can be provided to the one or more transistors to convert the input power to a suitable output using pulse width modulation techniques, or other suitable techniques.

In particular, the control system 108 can be configured to control the driver circuits 110 based at least in part on a predefined light control profile. The light control profile can specify one or more time periods during which the HINS light is to be emitted and/or one or more time periods during which the non-HINS light is to be emitted. In this manner, during the one or more time periods during which HINS light is to be emitted, control system 108 can control operation of one or more driver circuits 110 associated with the HINS LEDs 105 to cause such driver circuits 110 to provide a suitable output current to the HINS LEDs 105 to cause the HINS LEDs 105 to emit HINS light. Similarly, during the one or more time periods during which non-HINS light is to be emitted, control system 108 can control operation of one or more driver circuits 110 associated with the non-HINS LEDs 107 to cause such driver circuits 110 to provide a suitable output current to the non-HINS LEDs 107 to cause such non-HINS LEDs 107 to emit non-HINS light. In some implementations, the control system 108 may control one or more driver circuits such that one or more HINS LEDs 105 and one or more non-HINS LEDs 107 emit light simultaneously based at least in part on the light control profile.

As indicated above, the light control profile can specify a timing scheme for emission of HINS light and/or non-HINS light. In some implementations, the timing scheme can be predefined, such that HINS light and/or non-HINS light are emitted during one or more predefined time periods and/or time intervals. For instance, the one or more predefined time periods can be defined relative to an activation of the display device 106, backlight system 102 and/or the device. In some implementations, the timing scheme can be determined responsive to one or more signals or indications associated with the display device 106. The one or more signals or indications can be associated with a state of the display device 106. For instance, an idle state or a state of inactivity of the display device 106 can be detected, and HINS light can be emitted in response to such detection. In some implementations, the idle state can be detected based on a lack of user interaction with the display device 106 for some period of time. In some implementations, the idle state can be detected based on an absence of a user proximate the display device 106 (e.g., as detected by one or more motion sensors or other sensors associated with the display device 106). In some implementations, an activation of a screen saver by the display device 106 can trigger the emission of HINS light in accordance with the light control profile. In this manner, the HINS light can be emitted during at least a subset of the duration of the screen saver activation.

In some implementations, the device can be a separate and distinct component from the backlight system 102. In such implementations, the backlight system 102 may be associated with an additional device. As an example, the backlight system 102 can be implemented within a computer monitor and can be configured to provide backlighting for a display device 106 implemented within the computer monitor. The device can be an I/O device (e.g. keyboard, mouse, etc.) located proximate the computer monitor. In this manner, the light provided by such backlight system 102 can be directed toward the external device via the display device 106 associated with the backlight system 102.

Figure 3:
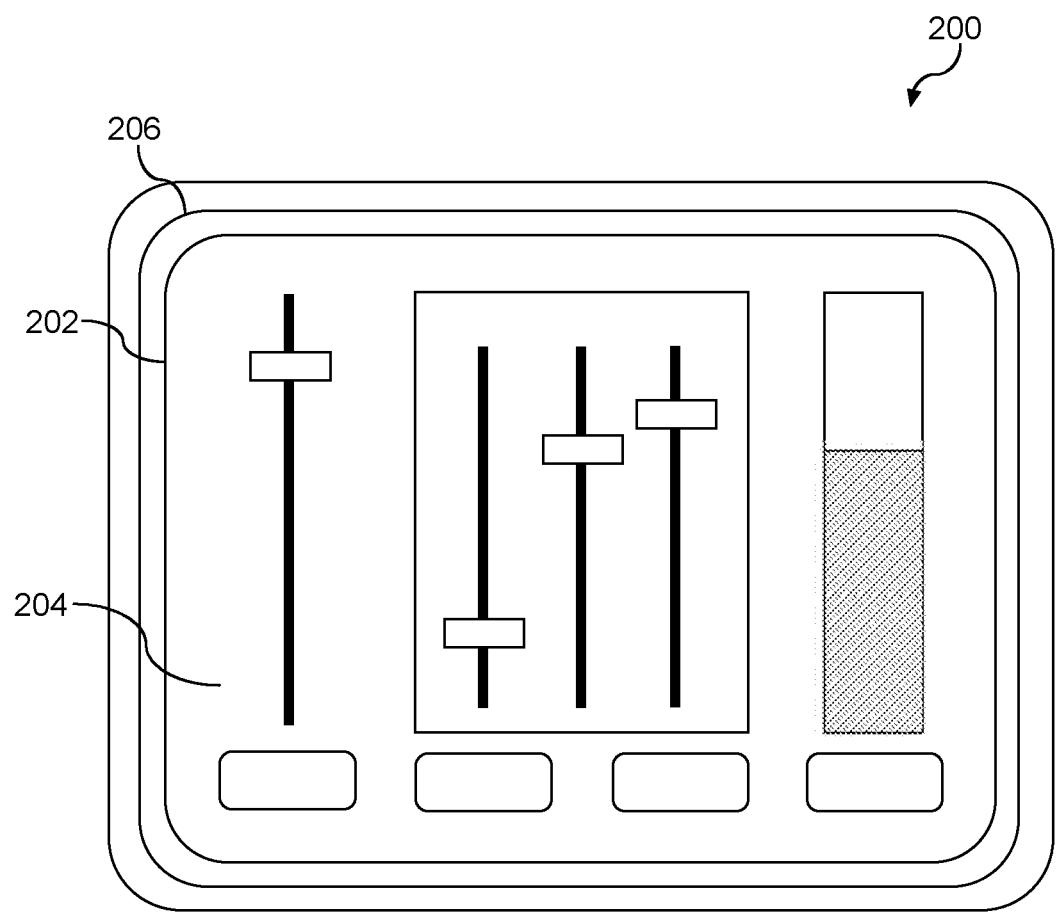
FIG. 3 depicts an example device according to example embodiments of the present disclosure.

FIG. 3 depicts an example device 200 according to example embodiments of the present disclosure. Device 200 includes a display device 202 configured to provide for display a user interface 204 associated with, for instance, a lighting control system. Display device 202 can be any suitable display device, such as an LCD device. In some implementations, display device 202 can be a touch device capable of receiving inputs from a user via contact of the display device 202 by an input device such as a user's hand, a stylus, etc. In this manner, the user can interact with the user interface 204 through one or more touch gestures performed on the display device 202. The user interface 204 can be any suitable user interface. For instance, the user interface 204 can be associated with a control application configured to control various aspects of one or more "smart home" appliances, such as a smart lighting system, a smart fan system, a smart alarm system, a smart air conditioning system, etc.

Device 200 can be associated with a backlight system 206 according to example aspects of the present disclosure. Backlight system 206 can be implemented within device 200. Backlight system 206 can be any suitable lighting system configured to provide a suitable backlight to display device 202. For instance, backlight system 206 can correspond to backlight system 102 of FIG. 2. In this manner, backlight system 206 can include a lighting array having a plurality of lighting elements (e.g., white LEDs and/or RGB LEDs) arranged in various suitable manners with respect to the device 200 to facilitate various suitable backlighting techniques. Backlight system 206 can further include one or more lighting elements configured to emit HINS light, and one or more lighting elements configured to emit non-HINS light.

Figure 4:
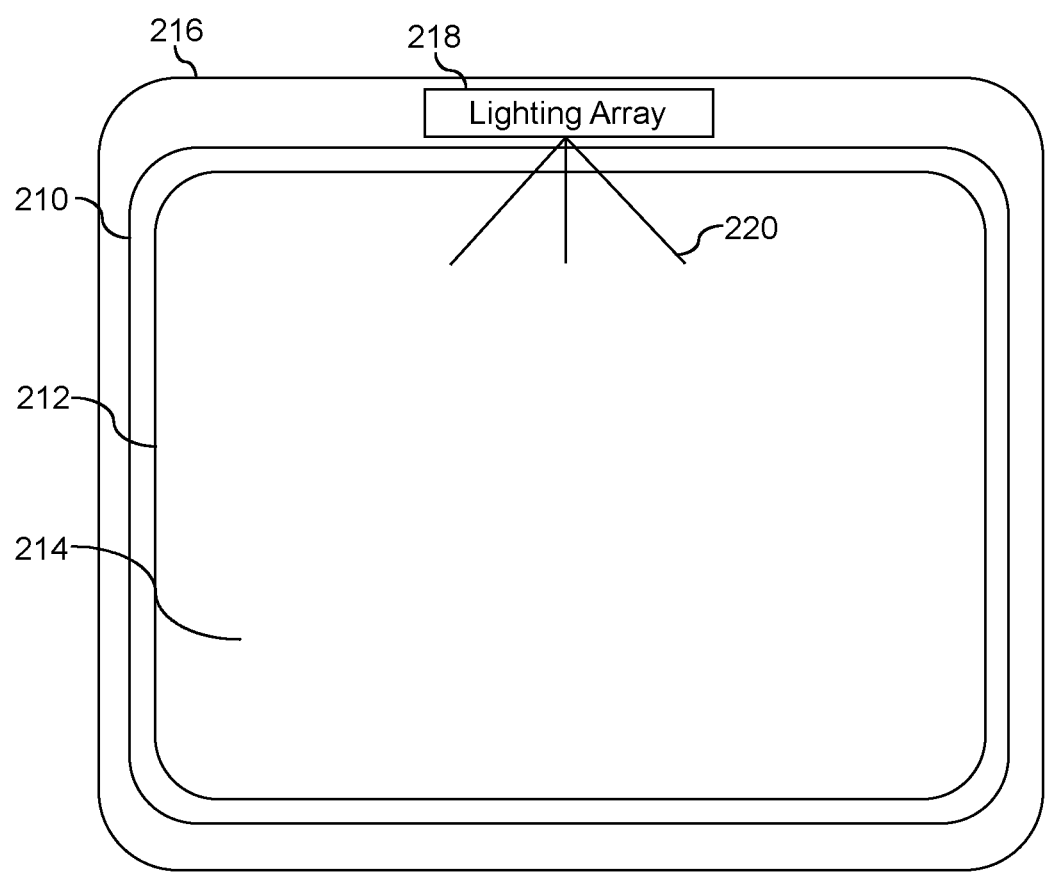
FIG. 4 depicts an example device according to example embodiments of the present disclosure.

FIG. 4 depicts an example device 210 according to example aspects of the present disclosure. The device 210 can be any suitable device, such as a smartphone. The device 210 can include a display device 212 configured to provide for display a user interface 214. The user interface 214 can correspond to the user interface 204 of FIG. 3, or other suitable user interface. The device 210 can further be associated with an external lighting system 216. The lighting system 216 can include a suitable lighting array 218. The lighting array 218 can correspond to the LED array 104 of FIG. 2 or other suitable lighting array. The lighting system 216 can be a separate and distinct component from the device 210. For instance, in some implementations, the lighting system 216 can be implemented within a casing configured to attach to or otherwise encompass at least a portion of the device 210.

The lighting array 218 can be configured to emit light 220 proximate the display device 212. In particular, the lighting array 218 can be configured to emit the light 220 in accordance with a light control profile according to example embodiments of the present disclosure. For instance, the lighting array 218 can be configured to emit HINS light during one or more time periods, and non-HINS light during one or more time periods based at least in part on the light control profile. In this manner, the light 220 can be emitted in a direction of the display device 212.

The device 210 can include a power supply configured to provide power to various components of the device 210. For instance, the power supply can provide power to the display device 212. In some implementations, the lighting system 216 can be powered by the power supply of the device 210, or other suitable power supply.

Figure 5:
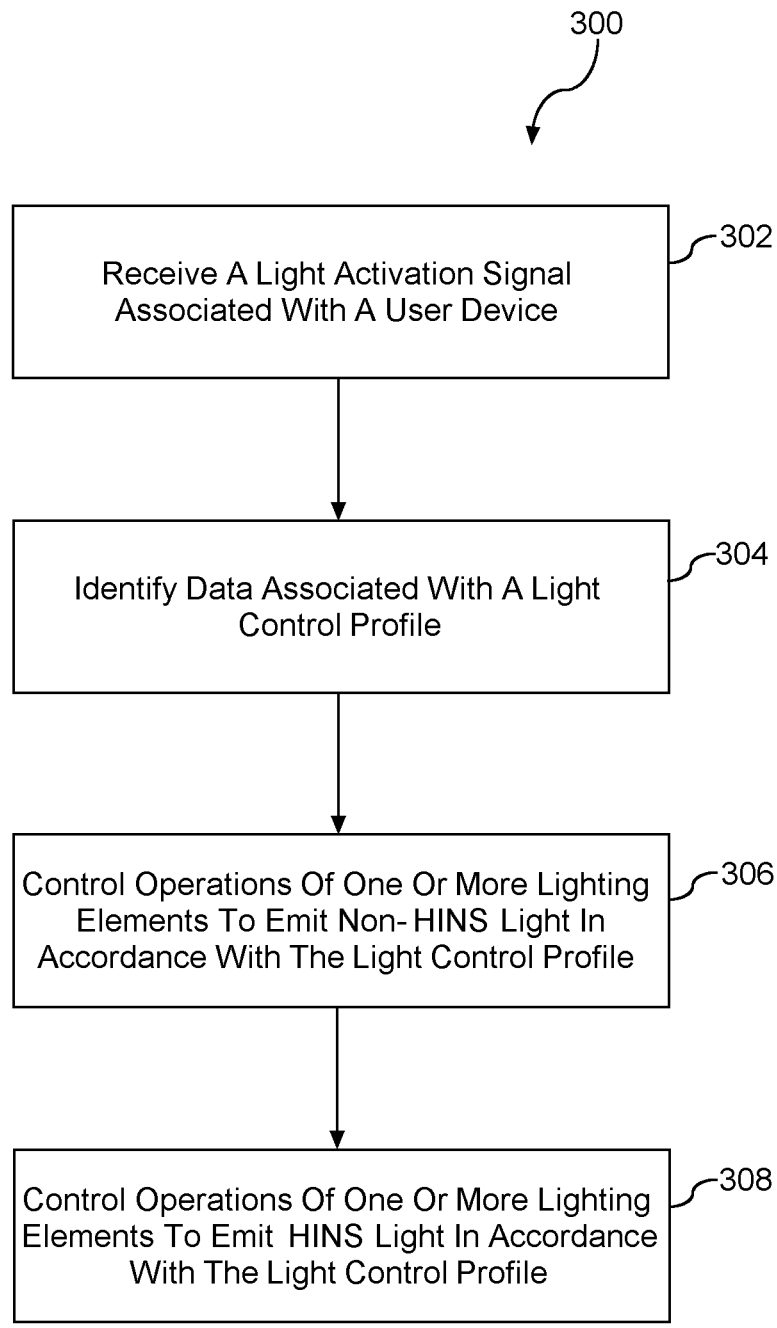
FIG. 5 depicts a flow diagram of a method of providing antimicrobial light according to example embodiments of the present disclosure.

FIG. 5 depicts a flow diagram of an example method (300) of providing antimicrobial lighting to a surface according to example embodiments of the present disclosure. Method (300) can be implemented by one or more devices, such as one or more of the devices depicted in FIG. 2. In addition, FIG. 4 depicts steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure.

At (302), method (300) includes receiving a light activation signal associated with a device. As indicated above, the device can be a user computing device, television, monitor, display device, I/O device, or other suitable device. In some implementations, the device can be any suitable device having one or more surfaces that may come into contact with a user. The light activation signal associated with the device can be associated with a presence of a user proximate the device, an activation of the device, an activation of a display device associated with the device, and/or a usage of the device by a user. For instance, in some implementations, the light activation signal can be associated with a detection of a presence of a user or other entity proximate the device by one or more sensors (e.g., motion sensors, etc.) associated with the device. In some implementations, the light activation signal can be associated with an activation of the device by the user (e.g., causing the interface to power on or "awake" from a sleep or idle mode, etc.). The activation of the device can be initiated, for instance, in response to an interaction with the device by a user.

At (304), method (300) can include accessing data associated with a light control profile. In some implementations, the data associated with the light control profile can be stored in one or more memory devices associated with the device and/or a lighting system associated with the device. As indicated, the light control profile can specify one or more time periods or time intervals during which HINS light is to be emitted and/or one or more time periods or intervals during which non-HINS light is to be emitted. For instance, the one or more time periods may be predetermined time periods (e.g., relative to reception of the light activation signal), or may be determined in real time, for instance, based at least in part on one or more states of the device. In some implementations, the light control profile may specify one or more trigger events, responsive to which HINS light and/or non-HINS light is to be emitted. The one or more trigger events can be associated with a state of the device. For instance, a trigger event can be associated with a level of activity of the device. As an example, a trigger event can occur when the device has been inactive for a predetermined amount of time. As another example, a trigger event can occur when a screen saver is activated by the device. As yet another example, a trigger event can occur when no user is detected proximate the device for some amount of time.

In some implementations, a trigger event can be associated with a detection of microbes on a surface of the device (e.g. display panel) by one or more sensors configured to detect microbes within an area. Such sensors can include, for instance, one or more microbe concentrating devices and/or one or more biosensors. For instance, the one or more sensors can provide an indication that a number of microbes greater than a threshold have been detected on the device surface. Such indication can be used as a trigger event to trigger the emission of HINS light to reduce or eliminate the detected microbes.

In some implementations, the light control can include trigger events and time periods or intervals during which HINS light is to be emitted. For instance, the light control profile can specify that HINS light is to be emitted for some time period or interval subsequent to the detection of a trigger event. In this manner, the timing of the HINS light emission can be determined in real time.

At (306), method (300) can include controlling operation of one or more lighting elements associated with the lighting system to emit non-HINS light in accordance with the light control profile. The lighting elements can include one or more white LEDs, one or more RGB LEDs, or other lighting elements. As indicated, the non-HINS light can be light having a wavelength within the visible spectrum, but not within the high-intensity narrow spectrum. Operation of the one or more lighting elements can be controlled by controlling one or more driver circuits associated with the one or more lighting elements to provide a suitable current to the one or more lighting elements. The one or more first lighting elements and the current can be determined to achieve a suitable color and/or intensity of light.

At (308), method (300) can include controlling operation of one or more lighting elements to emit HINS light in accordance with the light control profile. The operation of the one or more lighting elements can be controlled by controlling one or more driver circuits associated with the one or more lighting elements to provide a suitable current to the one or more second lighting elements. The one or more lighting elements and/or the current can be determined to achieve a suitable color and/or intensity of light.

In some implementations, the HINS light and the non-HINS light can be emitted simultaneously. For instance, the HINS light can be combined with the non-HINS light to create visible white light. In this manner, operation of at least a subset of the one or more lighting elements configured to emit non-HINS light and at least a subset of the one or more lighting elements configured to emit HINS light can be controlled to emit light simultaneously. In some implementations, at least one lighting element can be configured to emit both HINS light and non-HINS light.

Figure 6:
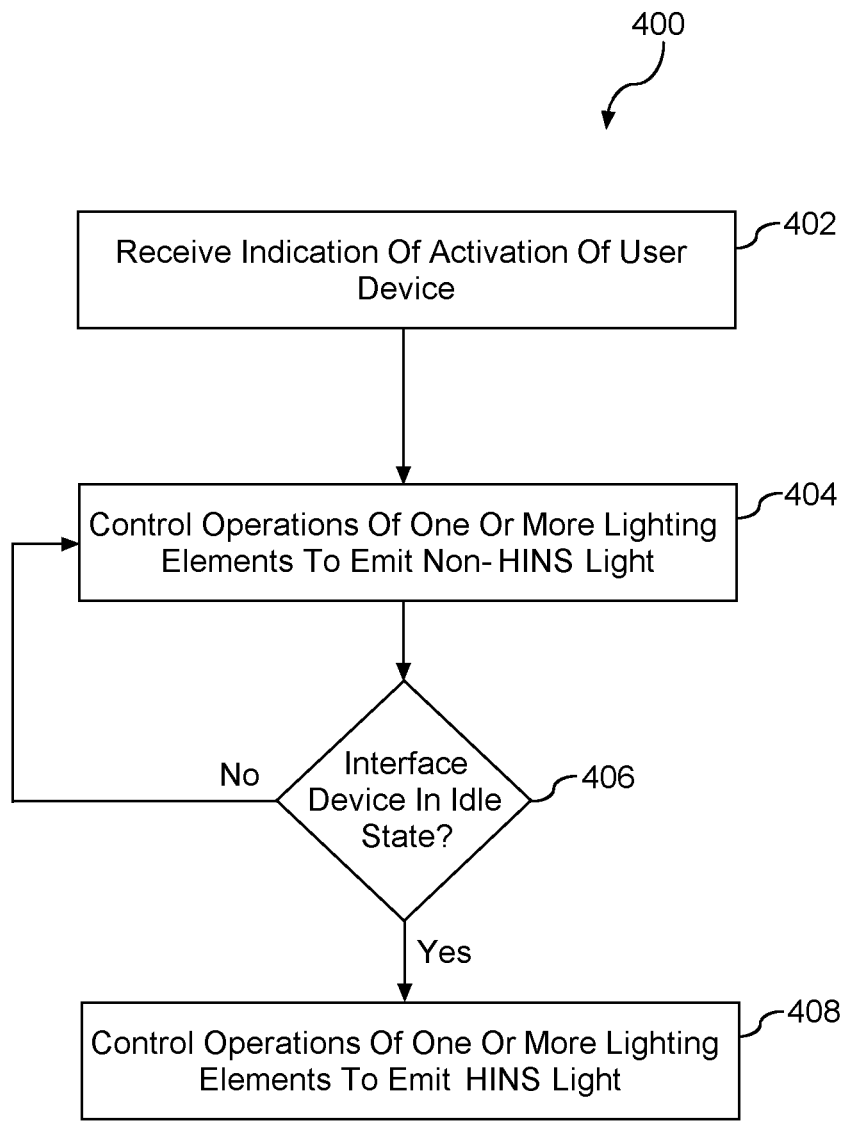
FIG. 6 depicts a flow diagram of a method of providing antimicrobial light according to example embodiments of the present disclosure.
Figure 7:
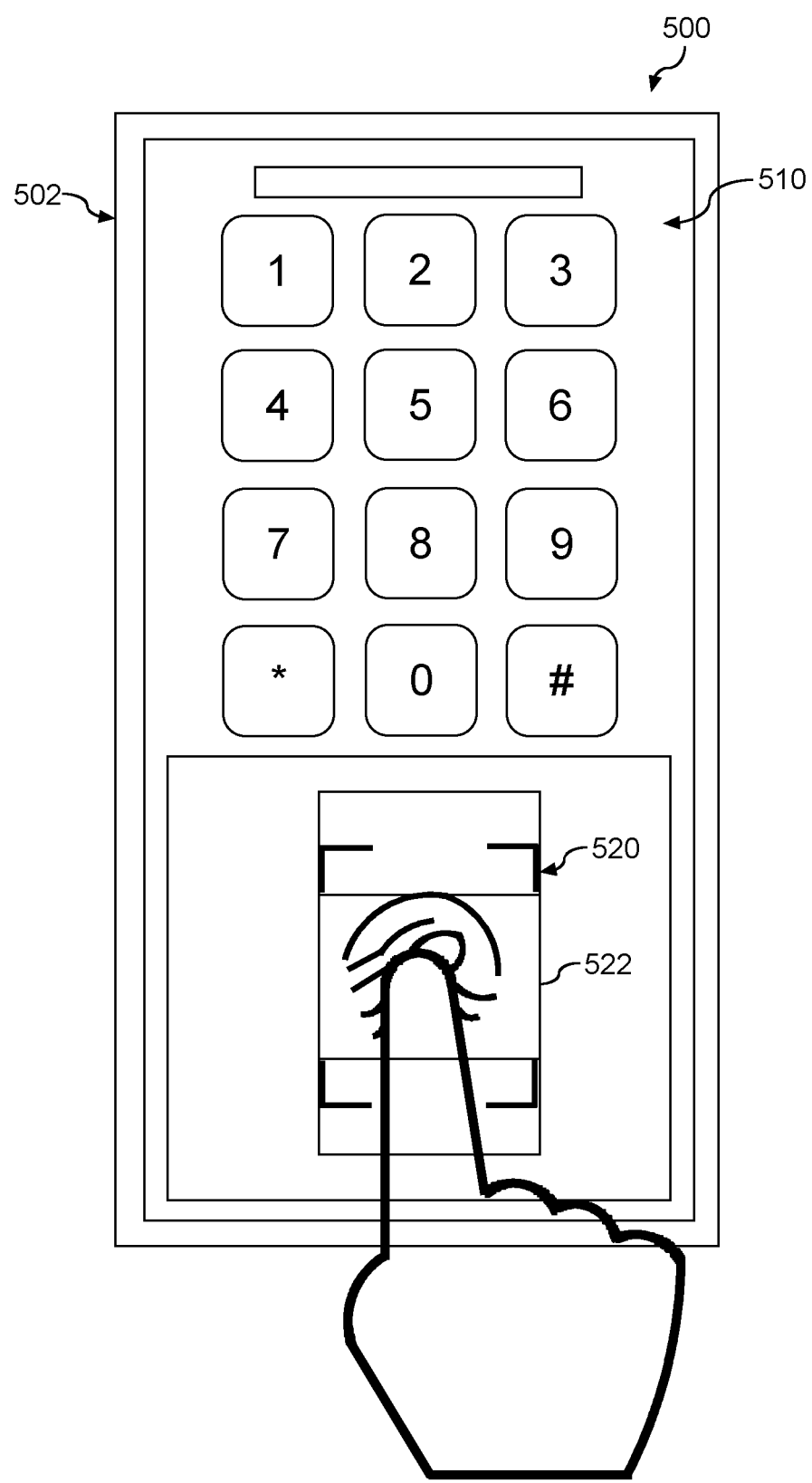
FIG. 7 depicts a front view of a human-machine interface device according to example embodiments of the present disclosure.
Figure 8:
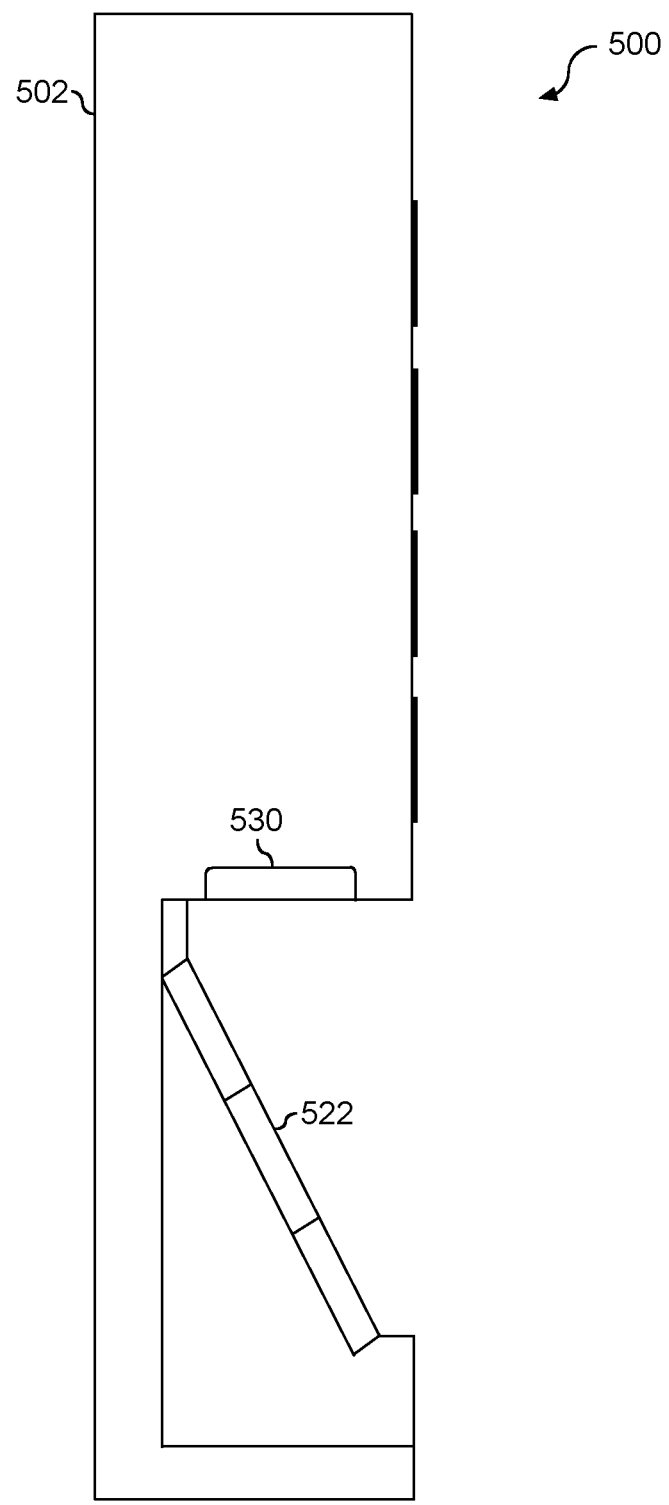
FIG. 8 depicts a side view of a human-machine interface device according to example embodiments of the present disclosure.
Figure 9:
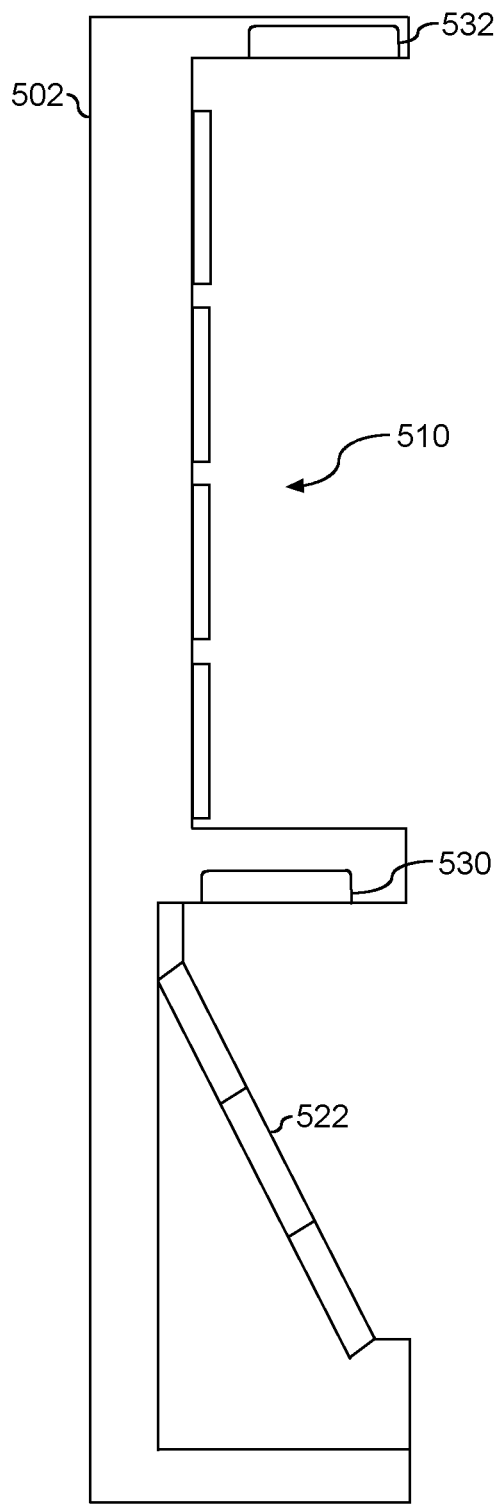
FIG. 9 depicts another side view of a human-machine interface device according to example embodiments of the present disclosure.
Figure 10:
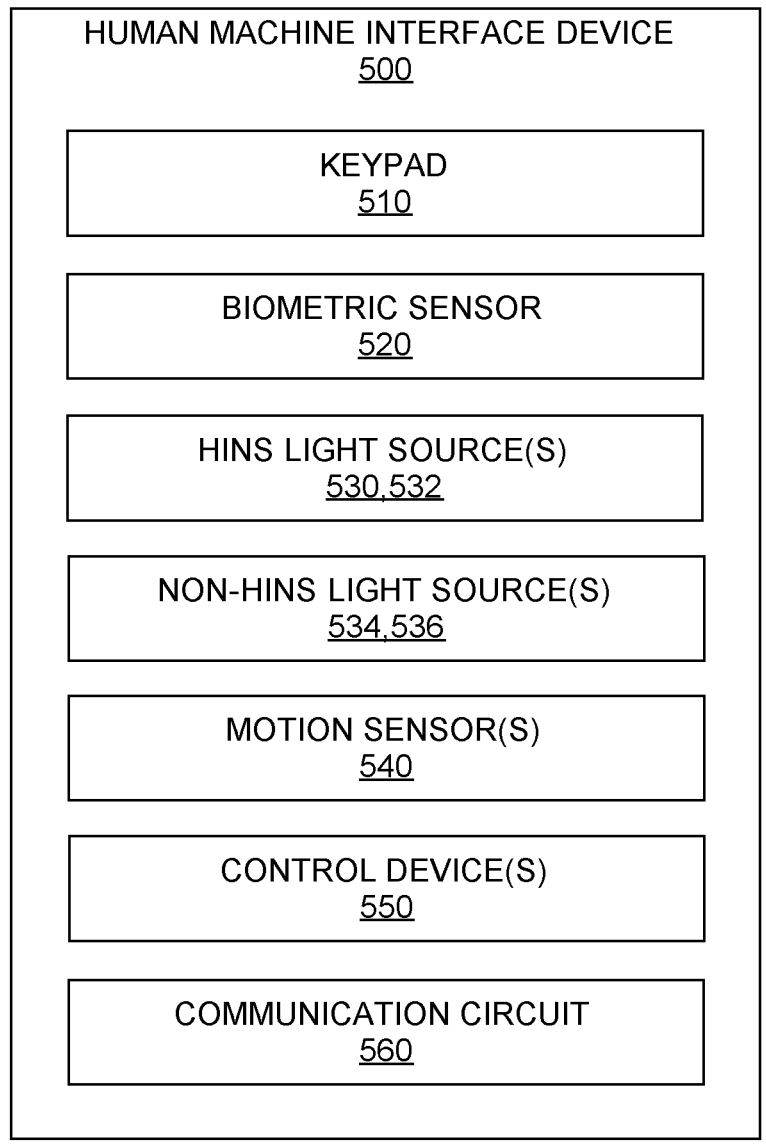
FIG. 10 depicts a block diagram of components of a human-machine interface device according to example embodiments of the present disclosure.

FIG. 6 depicts a flow diagram of an example method (400) of providing antimicrobial lighting to a surface according to example embodiments of the present disclosure. Method (400) can be implemented by one or more computing devices, such as one or more of the computing devices depicted in FIG. 2.

At (402), method (400) can include receiving an indication of an activation of a device. The activation of the device can be some action that causes a lighting system associated with a display device associated with the device to turn on.

At (404), method (400) can include controlling operation of one or more lighting elements associated with the lighting system to emit non-HINS light proximate the device (e.g. a display panel or other suitable surface associated with the device). For instance, the one or more lighting elements can be configured to emit any suitable color and/or intensity of light.

At (406), method (400) can include determining whether the device is in an idle state. For instance, determining whether the device is in an idle state can include determining whether a user is present proximate the device. If a user has not been present proximate the device for a threshold amount of time, it can be determined that the device is in an idle state. As another example, determining whether the device is in an idle state can include determining whether a screen saver has been activated by the device. If a screen saver is active on the device, it can be determined that the device is in an idle state. As yet another example, determining whether the device is in an idle state can include determining whether a user is currently using the device. For instance, if a user has not interacted with the device for some threshold amount of time, it can be determined that the device is in an idle state.

If the device is not in an idle state, method (400) can include returning to (404). If the device is in an idle state, method (400) can include controlling operation of one or more lighting elements associated with the lighting system to emit HINS light proximate the device. For instance, operation of the one or more lighting elements can be controlled to emit HINS light for some period of time. As another example, operation of the one or more lighting elements can be controlled to emit HINS light until the device is no longer in the idle state (e.g., based on the presence of a user, an interaction of a user with the device, a cessation of the screen saver, etc.).

Referring now to FIGS. 7-10, an example human machine interface (HMI) device 500 is provided according to example embodiments of the present disclosure. In some implementations, the HMI device 500 can be used to control access to an area. For example, the HMI device 500 can be associated with a door that is used to enter and exit a room. Alternatively, the HMI device can be used to control access to a device, such as an automated teller machine (ATM). It should be appreciated, however, that the HMI device 500 can be used for any suitable purpose.

In some implementations, the HMI device 500 can include a keypad 510. A housing 502 of the HMI device 500 can be configured to accommodate the keypad 510. The keypad 510 can include a plurality of buttons. In this manner, the plurality of buttons can be manipulated (e.g., pressed) by a user to enter a credential (e.g., passcode) needed to access to an area or device to which access is controlled by the HMI device 500.

In some implementations, the HMI device 500 can include a touch-screen instead of the keypad. The touch-screen can be configured to display a keypad having a plurality of buttons. In such implementations, a user can manipulate (e.g., touch) one or more buttons of the keypad to enter the credential needed to access the area or device.

As shown, the HMI device 500 can include a biometric sensor 520. The housing 502 of the HMI device 500 can be configured to accommodate the biometric sensor 520. In some implementations, the biometric sensor 520 can be configured to convert a biometric trait (e.g., fingerprint) of a user into an electrical signal. As will be discussed below in more detail, the electrical signal can be processed by one or more control devices 550 of the HMI device 500 to determine an identity of the user attempting to access an area or device to which access is controlled by the HMI device 500.

The HMI device 500 can include one or more HINS light sources 530 disposed within the housing 502. The one or more HINS light sources 530 can be configured to emit HINS light onto the biometric sensor 520. More particularly, the HINS light can be emitted onto a surface 522 of the biometric sensor 520 that users must contact (e.g., touch) in order for the biometric sensor 530 to convert the biometric trait into an electrical signal. In this manner, the HIMS light can inactivate microbes present on the surface 522 of the biometric sensor 520. In some implementations, the HMI device 500 can further include one or more HINS light sources 532 configured to emit HINS light onto the keypad 510. In this manner, the HINS light can inactivate microbes present on each of the plurality of buttons of the keypad 510.

In some implementations, the HMI device 500 include one or more non-HINS light sources 534 disposed within the housing 502. The one or more non-HINS light sources 534 can be configured to emit non-HINS light onto the biometric sensor 520. More particularly, the non-HINS light can be emitted onto the surface 522 of the biometric sensor 520. In this manner, the surface 522 of the biometric sensor 520 can be illuminated with the non-HINS light. In some implementations, the housing 502 of the HMI device 500 can further accommodate one or more non-HINS light sources 536. The non-HINS light sources 536 can be configured to emit non-HINS light onto the keypad 510. In this manner, each of the plurality of buttons of the keypad 510 can be illuminated with the non-HINS light.

In some implementations, the HMI device 500 can include one or more motion sensors 540 configured to detect presence of a user. It should be appreciated that the one or more motion sensors 540 can include any suitable type of motion sensor. For instance, in some implementations, the one or more motion sensors 540 can include infrared (IR) sensors.

Figure 11:
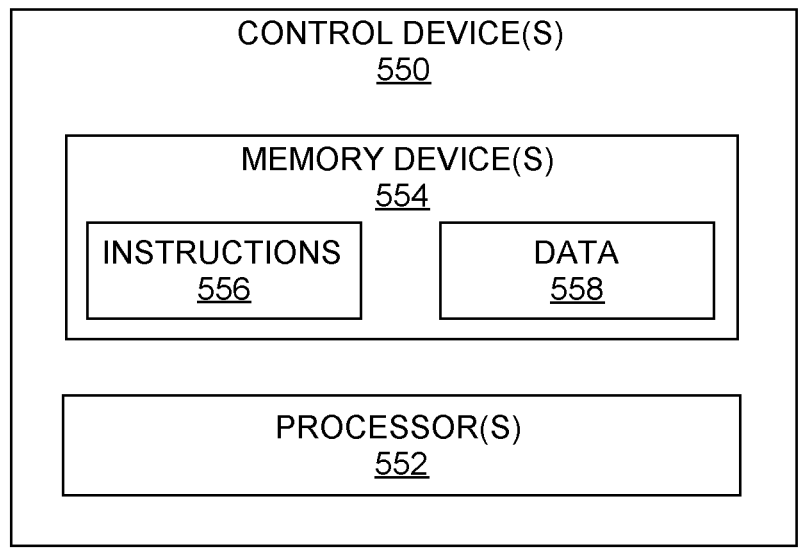
FIG. 11 depicts a block diagram of a control device according to example embodiments of the present disclosure.

Referring now to FIG. 11, a block diagram of suitable components of the control device(s) 550 of the HMI device 500 (FIGS. 7-10) are provided according to example embodiments of the present disclosure. As shown, the control device(s) 550 can include one or more processors 552 configured to perform a variety of computer-implemented functions (e.g., performing the methods, steps, calculations and the like disclosed herein). As used herein, the term "processor" refers not only to integrated circuits referred to in the art as being included in a computer, but also refers to a controller, microcontroller, a microcomputer, a programmable logic controller (PLC), an application specific integrated circuit (ASIC), a Field Programmable Gate Array (FPGA), and other programmable circuits.

As shown, the control device(s) 550 can include a memory device 554. Examples of the memory device 554 can include computer-readable media including, but not limited to, non-transitory computer-readable media, such as RAM, ROM, hard drives, flash drives, or other suitable memory devices. The memory device 554 can store information accessible by the processor(s) 552, including computer-readable instructions 556 that can be executed by the processor(s) 552. The computer-readable instructions 556 can be any set of instructions that, when executed by the processor(s) 552, cause the processor(s) 552 to perform operations. The computer-readable instructions 556 can be software written in any suitable programming language or can be implemented in hardware. In some implementations, the computer-readable instructions 552 can be executed by the processor(s) 552 to perform operations, such as controlling operation of the one or more HINS light sources 530, 532 and the one or more non-HINS light sources 534, 536.

In some implementations, the memory device 554 can store data 558 associated with controlling operation of the one or more HINS light sources 530, 532. Additionally, the data 558 can be associated with controlling operation of the one or more non-HINS light sources 534, 536. For instance, the data 558 can include one or more lighting control profiles. The one or more lighting control profiles can specify the manner in which the one or more HINS light sources 530, 532 and the one or more non-HINS light sources 534, 536 are to be operated.

In some implementations, the HMI device 500 can include a communication circuit 560. The communication circuit 560 can include associated electronic circuitry that can be used to communicatively couple the control device(s) 560 with other devices, such as control device(s) 550 associated with a user device (e.g., smartphone, tablet, laptop, etc.). In some implementations, the communication circuit 560 can allow the control device(s) 550 to communicate directly with the other devices. In other implementations, the communication circuit 560 can provide for communication with the other devices over a network.

The network can be any suitable type of network, such as a Power-Over-Ethernet (POE) network, a local area network (e.g., intranet), a wide area network (e.g., internet), a low power wireless network (e.g., Bluetooth Low Energy (BLE), Zigbee, etc.), or some combination thereof and can include any number of wired or wireless links. In general, communication over the network can be implemented via any type of wired or wireless connection, using a wide variety of communication protocols, encodings or formats, and/or protection schemes.

Example communication technologies used in accordance with example aspects of the present disclosure can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), Power over Ethernet, etc. Other suitable wired and/or wireless communication technologies can be used without deviating from the scope of the present disclosure.

Figure 12:
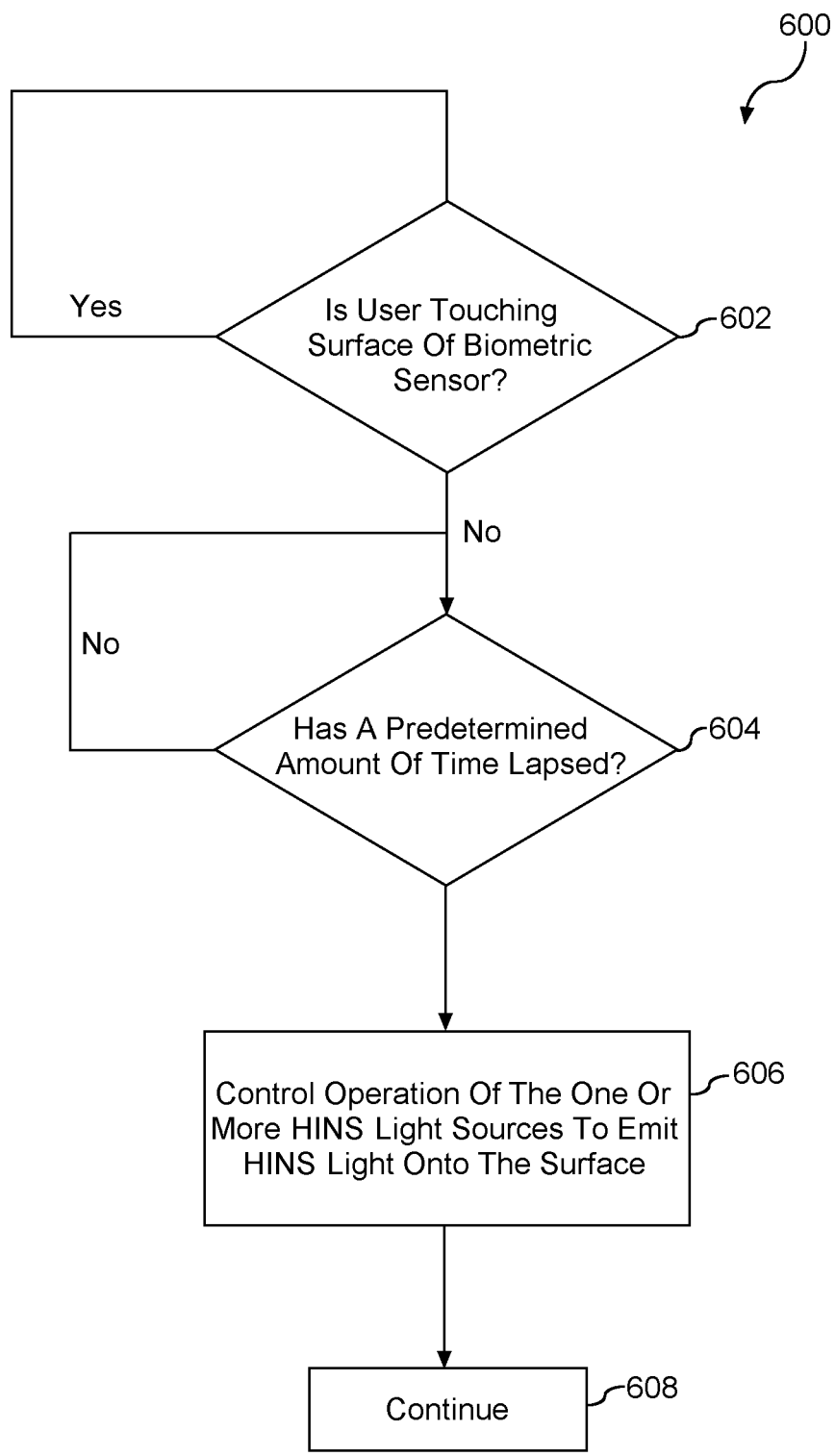
FIG. 12 depicts a flow diagram of a method of providing HINS light onto one or more surfaces of a human-machine interface device according to example embodiments of the present disclosure.

Referring now to FIG. 12, a flow diagram of a method 600 for providing antimicrobial lighting to a HMI device 500 according to example embodiments of the present disclosure. It should be appreciated that the method 600 can be implemented using the dimmer switch discussed above with reference to FIGS. 7-11. FIG. 12 depicts steps performed in a particular order for purposes of illustration and discussion. Those of ordinary skill in the art, using the disclosures provided herein, will understand that various steps of the method 600 may be adapted, modified, rearranged, performed simultaneously or modified in various ways without deviating from the scope of the present disclosure.

At (602), the method 600 includes obtaining, by one or more control devices of the HMI device, data indicative of whether a user is touching a surface of the biometric sensor users must contact in order for the biometric sensor to obtain the biometric trait (e.g., finger print) of the users. In example embodiments, the one or more control devices can determine whether the user is touching the surface of the biometric sensor based, at least in part, on whether the one or more control devices are receiving one or more electrical signals from the biometric sensor. If the one or more control devices are receiving one or more electrical signals indicative of a biometric trait, the method 600 remains at (602). Otherwise, the method 600 continues to (604).

At (604), the method 600 includes determining, by the one or more control devices, whether a predetermine amount of time has lapsed since the user was last detected touching the surface of the biometric sensor. If the one or more control devices determine the predetermined amount of time has lapsed, the method 600 proceeds to (606). Otherwise, the method 600 remains at (604) or reverts to (602) if the one or more control devices obtain data indicative of a user touching the surface of the biometric sensor.

At (606), the method 600 includes controlling, by the one or more control devices, operation of the one or more HINS light sources to illuminate the surface of the biometric sensor with HINS light. In some implementations, the method 600 can further include controlling, by the one or more control devices, operation of the one or more non-HINS light sources to illuminate the surface of the biometric sensor with non-HINS light. In this manner, the surface of the biometric sensor can be illuminated with a blend of HINS light and non-HINS light. In example embodiments, the one or more control devices can illuminate the surface of the biometric sensor with the blend of HINS light and non-HINS light for a predetermined amount. Furthermore, the one or more control devices can be configured to deactivate the one or more non-HINS light sources after the predetermined amount of time has lapsed. In this manner, only the one or more HINS light sources can continue to illuminate the surface of the biometric sensor.

At (608), the method 600 can continue. In some implementations, the one or more HINS light sources can continue to illuminate the surface of the biometric sensor until the one or more control devices obtain data indicative of a user touching the surface of the biometric sensor. Alternatively, the one or more control devices can continue to illuminate the surface of the biometric sensor with HINS light until one or more sensors configured to detect a level microbes present on the surface indicate the amount of microbes present on the surface is less than a threshold value.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An electronic device, comprising:
a display device comprising a display screen; and
a backlight system configured to provide backlight for the display device, the backlight system comprising one or more high intensity narrow spectrum (HINS) light sources configured to emit HINS light, the backlight system further comprising one or more non-HINS light sources configured to emit non-HINS light; and
one or more control devices configured to:
obtain data indicative of a trigger event;
access one or more light control profiles based on the data indicative of the trigger event; and
control operation of the one or more HINS light sources and the one or more non-HINS light sources based on the one or more light control profiles, wherein the data indicative of the trigger event comprises data indicative of a number of microbes present on the display screen being greater than a threshold value.

2. The electronic device of claim 1, wherein the one or more control devices are configured to obtain data from one or more motion sensors of the electronic device.

3. The electronic device of claim 2, wherein when the data obtained from the one or more motion sensors indicates presence of a user, the one or more control devices are configured to control operation of the one or more HINS light sources and the one or more non-HINS light sources such that the backlight comprises a blend of the HINS light and the non-HINS light.

4. The electronic device of claim 3, wherein when the data obtained from the one or more motion sensors no longer indicates presence of the user, the one or more control devices are configured to control operation of the one or more HINS light sources and the one or more non-HINS light sources to provide the blend of the HINS light and the non-HINS light for a predetermined amount of time.

5. The electronic device of claim 4, wherein when the predetermined amount of time lapses, the one or more control devices are configured to deactivate the one or more non-HINS light sources.

6. The electronic device of claim 1, wherein the HINS light has a wavelength ranging from about 380 nanometers (nm) to about 420 nm.

7. The electronic device of claim 1, wherein the HINS light has a wavelength of about 405 nm.

8. The electronic device of claim 1, wherein the display screen comprises a liquid crystal display (LCD) screen.

* * * * *